(12) United States Patent
Chu (10) Patent No.: US 10,537,346 B2
(45) Date of Patent: Jan. 21, 2020

(54) RETRIEVAL DEVICES AND RELATED METHODS OF USE

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 199 days.

(21) Appl. No.: 15/628,469

(22) Filed: Jun. 20, 2017

(65) Prior Publication Data

US 2017/0281205 A1 Oct. 5, 2017

Related U.S. Application Data

(63) Continuation of application No. 14/585,382, filed on Dec. 30, 2014, now Pat. No. 9,724,113.

(Continued)

(51) Int. Cl.
*A61B 17/221* (2006.01)
*A61B 17/22* (2006.01)
*A61B 17/50* (2006.01)

(52) U.S. Cl.
CPC ...... *A61B 17/221* (2013.01); *A61B 17/22031* (2013.01); *A61B 17/50* (2013.01);
(Continued)

(58) Field of Classification Search
CPC ....... A61B 17/22; A61B 17/50; A61B 17/221; A61B 17/22031; A61B 2017/2212; A61B 2017/2215
See application file for complete search history.

(56) References Cited

U.S. PATENT DOCUMENTS 4,222,380 A * 9/1980 Terayama ............. A61M 5/425
600/104
5,906,622 A 5/1999 Lippitt et al.
(Continued)

FOREIGN PATENT DOCUMENTS

EP 2 949 277 A1 12/2015
WO WO 98/48710 A1 11/1998
(Continued)

OTHER PUBLICATIONS

International Search Report and Written Opinion for International Application No. PCT/US2014/072650, dated Mar. 17, 2015 (13 pages).

*Primary Examiner* — Vi X Nguyen
(74) *Attorney, Agent, or Firm* — Bookoff McAndrews, PLLC (57) ABSTRACT

According to an embodiment of the present disclosure, a retrieval device may include a distally located end effector movable between a contracted state and an expanded state. The end effector may include a plurality of support members each including a passage. The end effector may also include a plurality of movable members. A first movable member may include a first portion extending into a first passage of the support member passages. The retrieval device may also include a proximally located handle assembly including a longitudinal actuator and a twisting actuator coupled to the plurality of movable members. The longitudinal actuator and twisting actuator may be configured to longitudinally move and twist the movable members without longitudinally moving and twisting the support members.

18 Claims, 7 Drawing Sheets

Related U.S. Application Data (60) Provisional application No. 61/923,446, filed on Jan. 3, 2014.

(52) U.S. Cl.
CPC ............. *A61B 2017/2212* (2013.01); *A61B 2017/2215* (2013.01); *A61B 2017/22035* (2013.01)

(56) References Cited

U.S. PATENT DOCUMENTS

| | | | |
|---|---|---|---|
| 5,924,175 A | 7/1999 | Lippitt et al. | |
| 6,159,220 A | 12/2000 | Gobron et al. | |
| 6,193,672 B1 * | 2/2001 | Clement | A61B 18/14 600/565 |
| 6,228,023 B1 | 5/2001 | Zaslavsky et al. | |
| 6,458,145 B1 | 10/2002 | Ravenscroft et al. | |
| 6,626,915 B2 | 9/2003 | Leveillee | |
| 7,041,108 B2 | 5/2006 | Lippitt et al. | |
| 7,169,154 B1 | 1/2007 | Que et al. | |
| 7,210,210 B2 | 5/2007 | Lippitt et al. | |
| 2001/0047169 A1 | 11/2001 | McGuckin et al. | |
| 2002/0133170 A1 | 9/2002 | Tsuruta | |
| 2003/0225419 A1 | 12/2003 | Lippitt et al. | |
| 2004/0059349 A1 * | 3/2004 | Sixto, Jr. | A61B 17/0643 606/139 |
| 2004/0092957 A1 | 5/2004 | Lippitt et al. | |
| 2007/0106304 A1 | 5/2007 | Hammack et al. | |
| 2008/0086149 A1 | 4/2008 | Diamant et al. | |
| 2009/0163896 A1 | 6/2009 | Kumate et al. | |
| 2013/0131688 A1 | 5/2013 | Schwartz | |
| 2015/0066047 A1 | 3/2015 | Chu et al. | |
| 2015/0066049 A1 | 3/2015 | Chu | |
| 2015/0148814 A1 | 5/2015 | Chu | |
| 2015/0164522 A1 | 6/2015 | Budiman et al. | |
| 2015/0190157 A1 | 7/2015 | Chu | |
| 2015/0190190 A1 | 7/2015 | Chu | |
| 2015/0196311 A1 | 7/2015 | Chu | |
| 2015/0327878 A1 | 11/2015 | Chu et al. | |

FOREIGN PATENT DOCUMENTS

| | | |
|---|---|---|
| WO | WO 99/16363 A1 | 4/1999 |
| WO | WO 2007/046355 | 4/2007 |
| WO | WO 2015/106131 | 7/2015 |

* cited by examiner

RETRIEVAL DEVICES AND RELATED METHODS OF USE

CROSS-REFERENCE TO RELATED APPLICATIONS

This application is a Continuation Application of U.S. patent application Ser. No. 14/585,382, filed Dec. 30, 2014, which claims the benefit of priority from U.S. Provisional Application No. 61/923,446, filed on Jan. 3, 2014, both of which are incorporated by reference herein in their entireties.

TECHNICAL FIELD

Various embodiments of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Further, lithotripsy and ureteroscopy, for example, are used to treat urinary calculi (e.g., kidney stones) in the ureter of a patient.

Retrieval devices may include end effectors for manipulating objects. An exemplary end effector may have a plurality of arms that support a front loop that forms when the end effector is opened. The size of the front loop may limit the size of an object that can be captured, repositioned, and/or released from the end effector. For some procedures, there may be a need to increase the size of a front loop of an end effector to facilitate the capturing, repositioning, and/or releasing of larger objects. It may also be desirable to have an end effector close back down to a low-profile state to facilitate insertion and withdrawal of the end effector into and from a target area, and/or to capture, reposition, and/or release smaller objects. Thus, there remains a need for retrieval devices with improved capabilities.

SUMMARY

Embodiments of the present disclosure relate to, among other things, retrieval devices and related systems and methods. Each of the embodiments disclosed herein may include one or more of the features described in connection with any of the other disclosed embodiments.

In one embodiment of the present disclosure, a retrieval device may include a distally located end effector movable between a contracted state and an expanded state. The end effector may include a plurality of support members each including a passage. The end effector may also include a plurality of movable members. A first movable member may include a first portion extending into a first passage of the support member passages. The retrieval device may also include a proximally located handle assembly including a longitudinal actuator and a twisting actuator coupled to the plurality of movable members. The longitudinal actuator and twisting actuator may be configured to longitudinally move and twist the movable members without longitudinally moving and twisting the support members.

Embodiments of the retrieval device may include one or more of the following features: a second portion of the first movable member may extend out of the first passage and into a second passage of the support member passages; the first movable member and a pair of adjacent support members may form an end effector loop; the longitudinal actuator and the twisting actuator may include a common actuator member for causing longitudinal moving and twisting of the movable members; a portion of one of the movable members may twist around a portion of another of the movable members; and a portion of each of the movable members may follow a helical path.

In another embodiment of the present disclosure, a retrieval device may include a distally located end effector movable between a contracted state and an expanded state. The end effector may include a plurality of support members each including a passage. The end effector may also include a plurality of movable members at least partially received in the passages. In the expanded state the movable members may be displaced longitudinally and twisted relative to the contracted state.

Embodiments of the retrieval device may include one or more of the following features: each of the movable members may include a proximal portion and a distal portion, wherein at least part of the proximal portion may be rotatable relative to at least part of the distal portion to generate torsion in the movable member when the movable member is twisted, and the movable members may be movable longitudinally relative to the support members; the torsion in the movable members may bias the distal portions of the movable members towards bent configurations; a sheath may be configured to receive the support members and the movable members, wherein each of the movable members may extend radially outwardly from a longitudinal axis of the retrieval device when in the bent configuration; a proximally located handle assembly may be configured to twist the movable members and move the movable members longitudinally relative to the support members; the handle assembly may be configured to rotate the movable members while moving the movable members longitudinally; the support members and the movable members may form a plurality of loops; and the plurality of loops may include a distal front loop and a plurality of proximal side loops.

In another embodiment of the present disclosure, a method for retrieving an object from a target area may include positioning a distally located end effector of a retrieval device at the target area with the distally located end effector in a contracted state. The end effector may include a plurality of support members each including a passage. The end effector may also include a plurality of movable members extending into the support member passages. The method may also include expanding the end effector by longitudinally extending and twisting the movable members without longitudinally extending and twisting the support members, to allow the object to enter the end effector.

Embodiments of the method may include one or more of the following features: the movable members may be twisted before being longitudinally extended; the movable members may be twisted after being longitudinally extended; the movable members may be twisted while being longitudinally extended; contracting the end effector by longitudinally retracting the end effector; and contracting the end effector by untwisting the movable members.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Overview

The present disclosure is drawn to retrieval devices and related systems and methods. Reference will now be made in detail to embodiments of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

Exemplary Embodiments

Figure 1:
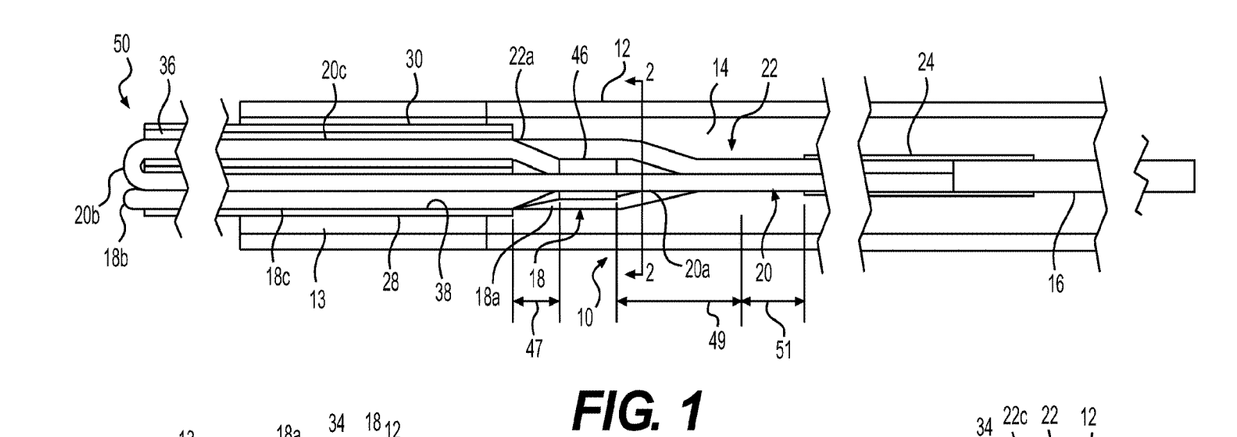
FIG. 1 is a side view of a retrieval device including an end effector in a retracted and contracted state, in accordance with embodiments of the present disclosure.
Figure 2:
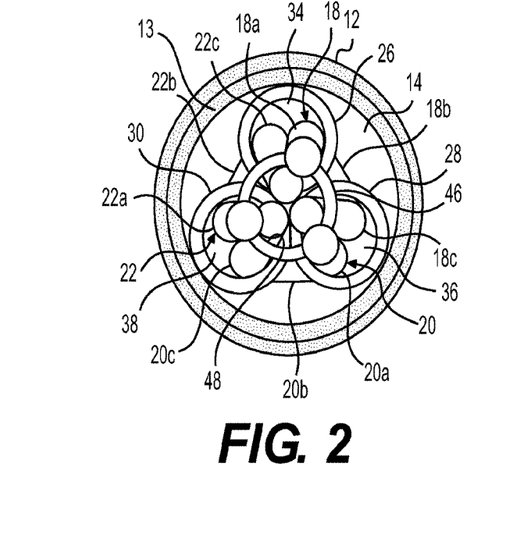
FIG. 2 is a cross-sectional view of the retrieval device of FIG. 1, in accordance with embodiments of the present disclosure.
Figure 3:
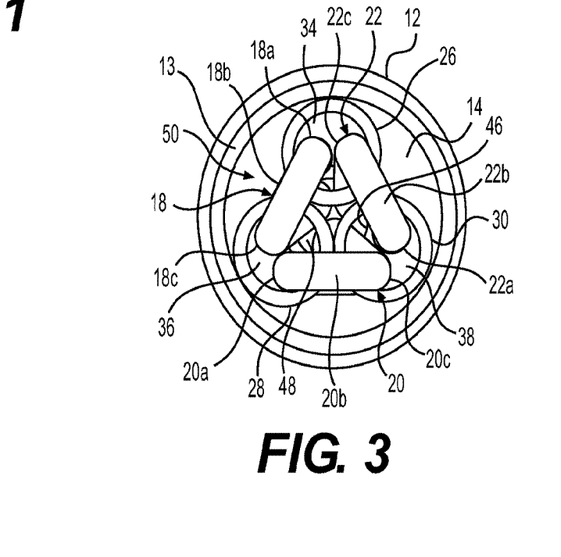
FIG. 3 is a distal end view of the retrieval device of FIG. 1, in accordance with embodiments of the present disclosure.

FIGS. 1-3 show portions of a retrieval device 10. The retrieval device 10 may include an outer sheath 12. The outer sheath 12 may include a lumen 14 extending longitudinally through the outer sheath 12. The outer sheath 12 may be, for example, a hollow tube of about 1.9 French, although the dimensions may differ based on the type of procedure being performed with the retrieval device 10. The outer sheath 12 may be made of a polymer material or combination of materials. A proximal portion of the outer sheath 12 may be made of a different material than a distal portion of the outer sheath 12. For example, the distal portion of the outer sheath 12 may be made of a material that is more flexible than the material of the proximal portion of the outer sheath 12.

The retrieval device 10 may also include a drive member 16. The drive member 16 may extend through the lumen 14. The drive member 16 may be elongated, and may include, for example, a wire, braid, shaft, and or any other suitable drive member configured to transfer translational and/or rotational forces from its proximal end to its distal end. The drive member 16 may have any suitable cross-sectional shape, including cylindrical, elliptical, polygonal, and/or irregular. The drive member 16 may be made of metals, polymers, or a combination of materials. It is also contemplated that the drive member 16 may have a diameter of approximately 0.0125 inches. The drive member 16 may have other diameters, however, depending on the type of procedure being performed with the retrieval device 10.

The retrieval device 10 may also include a first movable member 18, a second movable member 20, and a third movable member 22. The first movable member 18 may include a first leg 18a, a reverse or U-shaped bend 18b, and a second leg 18c. The second movable member 20 may include a first leg 20a, a reverse or U-shaped bend 20b, and a second leg 20c. The third movable member 22 may include a first leg 22a, a reverse or U-shaped bend 22b, and a second leg 22c. While three movable members 18, 20, and 22 are shown, one or more additional movable members may also be included.

Each of the movable members 18, 20, and 22 may be formed of any suitable material including, but not limited to, metals, polymers, or a combination of materials. For example, one or more of the movable members 18, 20, and 22 may be formed with a shape memory material, such as Nitinol, and may be treated to possess an internal bias causing one or more of the movable members 18, 20, and 22 to move radially outwardly away from the longitudinal axis of the outer sheath 12 in the absence of a constraining force. One or more of the movable members 18, 20, and 22 may be a wire having a diameter of about 0.003 inches, although other suitable diameters may alternatively be utilized.

Each of the movable members 18, 20, and 22 may have any suitable cross-sectional shape, including cylindrical, elliptical, polygonal, and/or irregular. One or more of the movable members 18, 20, and 22 may include a portion flattened, machined, extruded, drawn, and/or etched into a different profile than a remaining portion. One or more of the movable members 18, 20, and 22 may be slotted to allow deflection or directional bending. The exterior surfaces of one or more of the movable members 18, 20, and 22 may be roughened, notched, slotted, etched, sand-blasted, or otherwise modified to provide a better gripping surface.

The movable members 18, 20, and 22 may be attached to the drive member 16. For example, proximal ends of the first legs 18*a*, 20*a*, and 22*a* may be attached to the distal end of the drive member 16. The attachment may be provided by one or more of a splice joint, adhesives, melting, welding, crimping, and/or any other suitable attachment mechanism.

It is also contemplated that a sleeve 24 may be placed over the proximal portions of the first legs 18*a*, 20*a*, and 22*a*, and the distal portion of the drive member 16. The sleeve 24 may be made of a polytetrafluoroethylene like TEFLON. The sleeve 24 may be heat shrinkable onto the first legs 18*a*, 20*a*, and 22*a*, and the drive member 16. The sleeve 24 may have a length of about 11.5 cm, but it should be understood that the length and other sleeve dimensions may vary based on the type of procedure being performed with the retrieval device 10. The sleeve 24 may help gather the first legs 18*a*, 20*a*, and 22*a*, so the gathered portions may not spread radially outwardly when pushed distally by the drive member 16, giving the gathered portions added strength. The proximal portions of each of the first legs 18*a*, 20*a*, and 22*a* may contact the proximal portions of the other first legs. Longitudinal axes of the proximal portions of the first legs 18*a*, 20*a*, and 22*a* may be substantially parallel.

The retrieval device 10 may also include a first support member 26, a second support member 28, and a third support member 30. The support members 26, 28, and 30 may include lumens 34, 36, and 38 extending longitudinally therethrough, respectively. In one embodiment, at least one of the support members 26, 28, and 30 may be a tube. The support members 26, 28, and 30 may be disposed circumferentially about the longitudinal axis of the outer sheath 12. The longitudinal axes of the support members may be disposed at equal intervals circumferentially about the longitudinal axis. It should, however, be noted that any other suitable number of support members and spacing configurations may alternatively be utilized. Each of the support members 26, 28, and 30 may have any suitable cross-sectional shape, including cylindrical elliptical, polygonal, and/or irregular. One or more of the support members 26, 28, and 30 may include a portion flattened, machined, extruded, drawn, and/or etched into a different profile than a remaining portion. One or more of the support members 26, 28, and 30 may be slotted to allow deflection or directional bending. One or more of the support members 26, 28, and 30 may have an inner diameter of about 0.007 inches, a wall thickness of about 0.001 inches, and/or a length of about 19.5 millimeters, although other suitable dimensions may alternatively be utilized. The exterior surfaces of one or more of the support members 26, 28, and 30 may be roughened, notched, slotted, etched, sand-blasted, or otherwise modified to provide a better gripping surface. The support members 26, 28, and 30 may be made of any suitable material, including a polymer such as polyimide, or polyethylene terephthalate.

The movable members 18, 20, and 22 and the support members 26, 28, and 30 may be heat treated together, and the material for the movable members 18, 20, and 22 and the support members 26, 28, and 30 may be selected such that the support members 26, 28, and 30 will not melt during heat treatment of the movable members 18, 20, and 22. While three support members 26, 28, and 30 are shown, one or more additional support members may be used.

Proximal portions of the support members 26, 28, and 30 may extend through the lumen 14, and may be covered by the outer sheath 12. For example, a length of about 10 millimeters of one or more of the support members 26, 28, and 30 may be covered by the outer sheath 12, leaving a length of about 9.5 millimeters exposed distal to the outer sheath 12. Each of the support members 26, 28, and 30 may contact the other two support members. For example, each of the proximal portions of the support members 26, 28, and 30 may contact the proximal portions of the other two support members, such that the support members 26, 28, and 30 may have a triangular arrangement around the longitudinal axis of the outer sheath 12 as shown in FIGS. 2 and 3. Longitudinal axes of the support members 26, 28, and 30 may form vertices of a triangle, and portions of the longitudinal axes may be parallel.

Distal portions of the support members 26, 28, and 30 may extend distally out of the lumen 14 and away from the distal end of the outer sheath 12. The distal portions may be configured to move towards and away from the longitudinal axis of the outer sheath 12. The number of support members 26, 28, and 30 may be equal to the number of movable members 18, 20, and 22.

Each of the three support members 26, 28, and 30 may be coupled to the outer sheath 12. For example, proximal ends of the support members 26, 28, and 30 that are covered by the distal end of the outer sheath 12 may be coupled to the distal end of the outer sheath 12 by an adhesive 13, such as an ultraviolet light curable adhesive or cyanoacrylate. Additionally or alternatively, the distal end of the outer sheath 12 may be heat shrunk onto the proximal ends of the support members 26, 28, and 30. The coupling may keep the proximal ends of the support members 26, 28, and 30 stationary relative to the distal end of outer sheath 12, while allowing the distal ends of the support members 26, 28, and 30 to move relative to the distal end of the outer sheath 12 and relative to one another.

The first leg 18*a* may extend distally from the drive member 16, and may enter the lumen 34 at the proximal end of the first support member 26. The first leg 18*a* may extend distally through the lumen 34, and may exit the lumen 34 at the distal end of the first support member 26. There the first leg 18*a* may transition into the bend 18*b*. The bend 18*b* may transition into the second leg 18*c*. The second leg 18*c* may enter the lumen 36 at the distal end of the second support member 28. The second leg 18*c* may extend proximally through the lumen 36, and may exit the lumen 36 at the proximal end of the second support member 28.

The first leg 20*a* may extend distally from the drive member 16, and may enter the lumen 36 at the proximal end of the second support member 28. The first leg 20*a* may extend distally through the lumen 36, and may exit the lumen 36 at the distal end of the second support member 28. There the first leg 20*a* may transition into the bend 20*b*. The bend 20*b* may transition into the second leg 20*c*. The second leg 20*c* may enter the lumen 38 at the distal end of the third support member 30. The second leg 20*c* may extend proximally through the lumen 38, and may exit the lumen 38 at the proximal end of the third support member 30.

The first leg 22*a* may extend distally from the drive member 16, and may enter the lumen 38 at the proximal end of the third support member 30. The first leg 22*a* may extend distally through the lumen 38, and may exit the lumen 38 at the distal end of the third support member 30. There the first leg 22*a* may transition into the bend 22*b*. The bend 22*b* may transition into the second leg 22*c*. The second leg 22*c* may enter the lumen 34 at the distal end of the first support member 26. The second leg 22*c* may extend proximally through the lumen 34, and may exit the lumen 34 at the proximal end of the first support member 26.

Alternatively, it is contemplated that the first leg 18*a* may extend distally through the first support member 26, and the second leg 18c may extend proximally through the third support member 30. The first leg 20a may extend distally through the second support member 28, and the second leg 20c may extend proximally through the first support member 26. The first leg 22a may extend distally through the third support member 30, and the second leg 22c may extend proximally through the second support member 28.

Distal ends of the second legs 18c, 20c, and 22c may be coupled by a coupler 46. The coupler 46 may be a tube, and may include a lumen 48 configured to receive distal ends of the second legs 18c, 20c, and 22c. The second legs 18c, 20c, and 22c may be attached to each other within the coupler 46. One or more of the second legs 18c, 20c, and 22c may be attached to the coupler 46. For example, one of more of the second legs 18c, 20c, and 22c may be attached to the coupler 46 by adhesive, melting, welding, friction fit, heat-shrinking the coupler 46, and/or any other suitable form of attachment. Portions of the first legs 18a, 20a, and 22a may extend along the side of the coupler 46, and may contact the exterior surface of the coupler 46. The coupler 46 may space portions of the first legs 18a, 20a, and 22a apart from the longitudinal axis of the outer sheath 12, to help guide the first legs 18a, 20a, and 22a into the support members 26, 28, and 30.

The movable members 18, 20, and 22, and the support members 26, 28, and 30, may form an end effector 50. The end effector 50 may be a basket 52. In FIGS. 1-3, the end effector 50 is shown in a retracted and contracted state. The end effector 50 may be moved into its retracted and contracted state by moving the drive member 16 proximally relative to the outer sheath 12. In the retracted and contracted state, the bends 18b, 20b, and 22b may be at or adjacent to the distal ends of the support members 26, 28, and 30. Distal ends of the first legs 18a, 20a, and 22a and the second legs 18c, 20c, and 22c may be positioned within the lumens 34, 36, and 38 of the support members 26, 28, and 30. The longitudinal axes of the support members 26, 28, and 30 may be substantially parallel, and both proximal and distal portions of each of the support members 26, 28, and 30 may be in contact the other support members. Portions of the first legs 18a, 20a, and 22a and the second legs 18c, 20c, and 22c in the lumens 34, 36, and 38 may be substantially parallel. The support members 26, 28, and 30, and/or the outer sheath 12 may counteract the inherent bias in the movable members 18, 20, and 22, keeping portions of the movable members 18, 20, and 22 from bending radially outwardly from the longitudinal axis of the outer sheath 12.

In the retracted and contracted state, the distal end of the coupler 46 may be spaced from the proximal ends of the support members 26, 28, and 30 by a distance 47. The distance 47 may be about 1 millimeter, although other distances may also be used. The proximal end of the coupler 46 may be spaced from the distal end of the sleeve 24 by a distance including a distance 49 and a distance 51. The distances 49 and 51 may total to about 16 millimeters, although other distances may also be used. For example, the distance 49 may be about 12 to 13 millimeters, while the distance 51 may be about 3 to 4 millimeters. The distances 47, 49, and 51 may vary based on the procedure being performed with the retrieval device 10.

Figure 4:
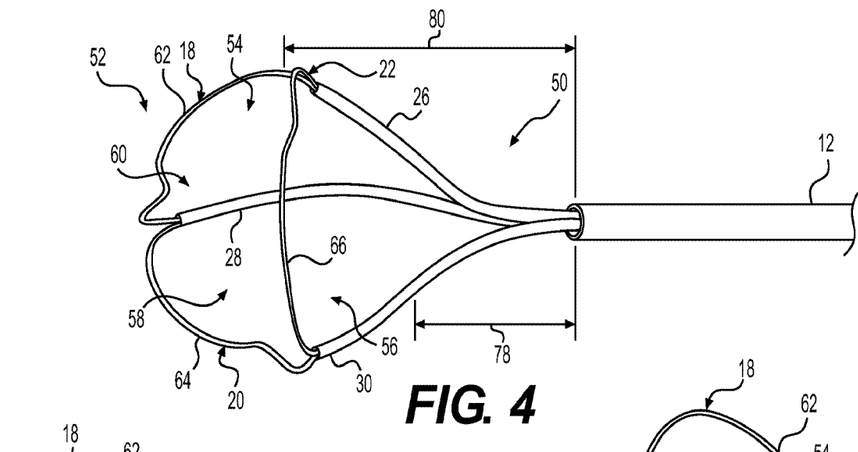
FIG. 4 is a perspective view of the retrieval device of FIG. 1 in an extended and expanded state, in accordance with embodiments of the present disclosure.
Figure 5:
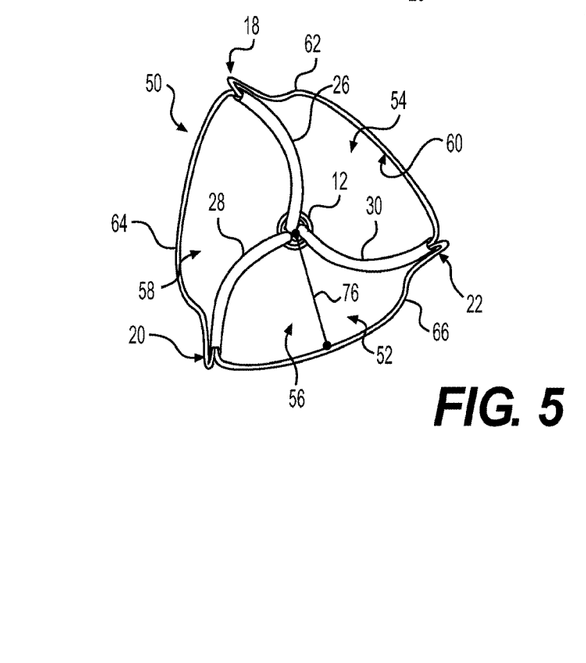
FIG. 5 is a distal end view of the retrieval device of FIG. 1 in the extended and expanded state, in accordance with embodiments of the present disclosure.

In FIGS. 4 and 5, the retrieval device 10 is shown with the end effector 50 in an extended and expanded state. In the extended and expanded state, portions of the movable members 18, 20, and 22 may be exposed from the distal ends of the support members 26, 28, and 30 and the outer sheath 12. Once exposed, one or more of the movable members 18, 20, and 22 may move radially outwardly from the longitudinal axis of the outer sheath 12 due to inherent radially outward biasing in one or more of the movable members 18, 20, and 22. Radially outward movement of one or more of the movable members 18, 20, and 22 may cause a corresponding radially outward movement of the support members 26, 28, and 30.

The exposed portions of the movable members 18, 20, and 22 may form bridges 62, 64, and 66 between the distal ends of the support members 26, 28, and 30. Each bridge may extend distally from the distal end of a given support member, and may be received in the distal end of an adjacent support member. The bridges 62, 64, and 66 may be formed by distal portions of the first legs 18a, 20a, and 22a, the bends 18b, 20b, and 22b, and distal portions of the second legs 18c, 20c and 22c.

Each bridge and its corresponding two support members may form a side loop of the end effector 50. Three side loops 54, 56, and 58 are shown in FIGS. 4 and 5. The bridges 62, 64, and 66 may form a front loop 60 of the end effector 50. Materials may enter the end effector 50 through one or more of the front loop 60 and the side loops 54, 56, and 58. By adding additional movable members and support members, additional side loops can be created.

The drive member 16 may be moved distally relative to the outer sheath 12 to extend the end effector 50, allowing the end effector 50 to move to its extended and expanded state due to inherent radially outward biasing in one or more of the movable members 18, 20, and 22. Extension and expansion of the end effector 50 may occur in phases. Starting from the retracted and contracted state shown in FIG. 1, a first phase of the extension and expansion of the end effector 50 may begin with movement of the drive member 16 distally relative to the outer sheath 12 and the support members 26, 28, and 30. The relative movement of the drive member 16 may cause the movable members 18, 20, and 22 and the coupler 46 to move distally relative to the outer sheath 12. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move distally relative to the outer sheath 12 and support members 26, 28, and 30 during the first phase. Proximal portions of the first legs 18a, 20a, and 22a and second legs 18c, 20c, and 22c may enter the lumens 34, 36, and 38 of the support members 26, 28, and 30 at the proximal ends of the support members 26, 28, and 30. Distal portions of the first legs 18a, 20a, and 22a, bends 18b, 20b, and 22b, and second legs 18c, 20c, and 22c may emerge from, or extend further out from, the distal ends of the support members 26, 28, and 30. The exposed portions of the movable members 18, 20, and 22 may form the bridges 62, 64, and 66, and the lengths of the bridges 62, 64, and 66 may grow as the exposed lengths of the movable members 18, 20, and 22 grow. As the bridges 62, 64, and 66 grow, distal portions of the movable members 18, 20, and 22, and the support members 26, 28, and 30, may expand radially outwardly from the longitudinal axis of the outer sheath 22. The front loop 60 and side loops 54, 56, and 58 may grow in size.

The coupler 46 may move with the movable members 18, 20, and 22 relative to the outer sheath 12 and support members 26, 28, and 30. When the coupler 46 has traveled the distance 47 relative to the outer sheath 12 and support members 26, 28, and 30, further distal movement of the coupler 46 may be halted as the coupler 46 reaches a point where it prevents further spreading of the second legs 18c, 20c, and 22c, thus preventing the second legs 18c, 20c, and 22c from entering the lumens 34, 36, and 38 of the support members 26, 28, and 30. At the end of the first phase of extension and expansion, the bends 18b, 20b, and 22b may each be spaced from distal ends of the support members 26, 28, and 30 by the distance 47.

A second phase of the extension and expansion of the end effector 50 may begin after distal movement of the coupler 46 has been halted. During the second phase, further distal movement of the drive member 16 relative to the outer sheath 12 and support members 26, 28, and 30 may drive distal movement of the first legs 18a, 20a, and 22a relative to the outer sheath 12 and support members 26, 28, and 30. During the second phase, the second legs 18c, 20c, and 22c may remain fixed relative to the support members 26, 28, and 30. The first legs 18a, 20a, and 22a may be increasingly exposed from the distal ends of the support members 26, 28, and 30, thereby increasing the lengths of the bridges 62, 64, and 66. Distal portions of the movable members 18, 20, and 22, and the support members 26, 28, and 30, may expand radially outwardly. The front loop 60 and the side loops 54, 56, and 58 may also expand in size.

Extension and expansion in the second phase may continue over the distance 49. Once the first legs 18a, 20a, and 22a have traveled the distance 49, distal movement of the drive member 16 may halt. Distal movement of the drive member 16 may be halted where the distal end of the sleeve 24 prevents the first legs 18a, 20a, and 22a from spreading far enough apart to enter the proximal ends of the support members 26, 28, and 30. Additionally or alternatively, distal movement may halt due to operation of a handle assembly of the retrieval device 10, such as a handle assembly 200 described further below.

Moving the end effector 50 back to the retracted and contracted state may be accomplished by moving the drive member 16 proximally relative to the outer sheath 12 and support members 26, 28, and 30. Movement from the extended and expanded state to the retracted and contracted state may also occur in phases. A first phase of the retraction and contraction of the end effector 50 may begin with the drive member 16 moving proximally relative to the outer sheath 12. This may cause the first legs 18a, 20a, and 22a to move proximally relative to the outer sheath 12 and support members 26, 28, and 30. Distal portions of the first legs 18a, 20a, and 22a may enter the lumens 34, 36, and 38 at the distal ends of the support members 26, 28 and 30. The second legs 18c, 20c, and 22c, and the coupler 46 may remain stationary relative to the support members 26, 28, and 30. The lengths of the bridges 62, 64, and 66 may decrease. The first legs 18a, 20a, and 20a, second legs 18c, 20c, and 22c, and support members 26, 28, and 30 may move radially inwardly. Thus, the front loop 60 and the side loops 54, 56, and 58 may decrease in size.

The first phase of the retraction and contraction of the end effector 50 may take place over the distance 49. Once the distance 49 has been covered, a second phase of the retraction and contraction may take place with continued movement of the drive member 16 proximally relative to the outer sheath 12 and the support members 26, 28, and 30. The continued movement may cause the movable members 18, 20, and 22 and the coupler 46 to move distally relative to the outer sheath 12 and support members 26, 28, and 30. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move proximally relative to the outer sheath 12 and support members 26, 28, and 30 during the second phase. Proximal portions of the first legs 18a, 20a, and 22a and second legs 18c, 20c, and 22c may exit the lumens 34, 36, and 38 of the support members 26, 28, and 30 at the proximal ends of the support members 26, 28, and 30. Distal portions of the first legs 18a, 20a, and 22a, bends 18b, 20b, and 22b, and second legs 18c, 20c, and 22c may enter into, or move further past, the distal ends of the support members 26, 28, and 30. The lengths of the bridges 62, 64, and 66 may decrease as the exposed lengths of the movable members 18, 20, and 22 decrease. As the bridges 62, 64, and 66 shrink, distal portions of the movable members 18, 20, and 22, and the support members 26, 28, and 30, may contract radially inwardly toward the longitudinal axis of the outer sheath 22. The front loop 60 and side loops 54, 56, and 58 may also shrink in size.

The coupler 46 may move with the movable members 18, 20, and 22 relative to the outer sheath 12 and support members 26, 28, and 30. When the coupler 46 has traveled the distance 47 relative to the outer sheath 12 and support members 26, 28, and 30, further proximal movement of the coupler 46 may be halted as the bends 18b, 20b, and 22b reach a point where they prevent further proximal movement of the movable members 18, 20, and 22. Additionally or alternatively, further movement may be halted by operation of a handle assembly of the retrieval device 10, such as the handle assembly 200 described further below. At the end of the second phase of retraction and contraction, the state shown in FIG. 1 is attained.

Figure 7:
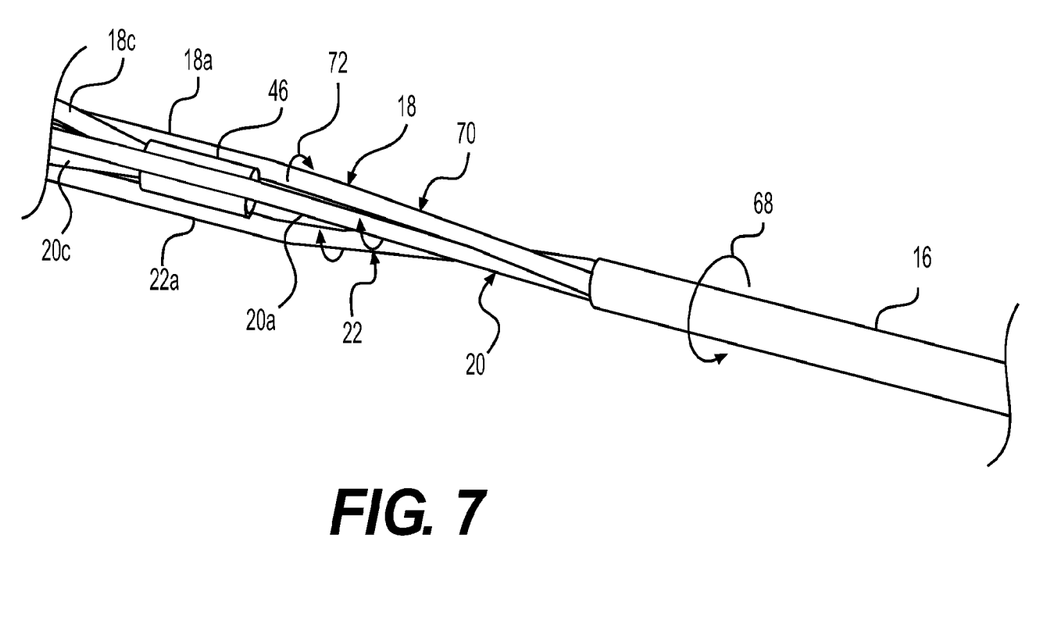
FIG. 7 is a perspective view of a portion of the retrieval device of FIG. 1, in accordance with embodiments of the present disclosure.

As shown in FIG. 7, the drive member 16 may be rotated about its longitudinal axis. Rotation 68 of the drive member 16 may twist the movable members 18, 20, and 22, causing portions of the first legs 18a, 20a, and 22a to form into a twisted section 70. In the twisted section 70, the movable members 18, 20, and 22 may follow a helical path. Continued rotation of the drive member 16 in the first direction may increase the twist. Rotating the drive member 16 in a second direction, opposite the first direction, may decrease the twist. FIG. 1 shows the device 10 without any twisting. Rotating the drive member 16 may also cause torsion or twisting 72 in each of the movable members 18, 20, and 22 about their respective longitudinal axes. Continued rotation of the drive member 16 in the first direction may cause the torsion or twisting 72 to increase. Rotating the drive member 16 in the second direction may cause the torsion or twisting 72 to decrease. The bends 18b, 20b, and 22b and the second legs 18c, 20c, and 22c may not become twisted due to their engagement with the support members 26, 28, and 30 and/or the coupler 46. The twisting and/or torsion may enhance or increase the inherent radially outward bias present in the movable members 18, 20, and 22.

Figure 6:
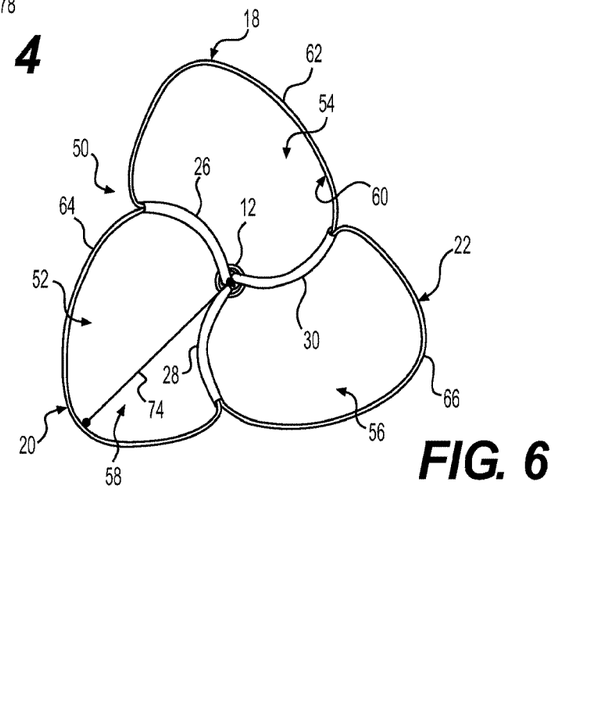
FIG. 6 is a distal end view of the retrieval device of FIG. 1 in another extended and expanded state, in accordance with embodiments of the present disclosure.

As shown in FIG. 6, due to the rotation 68 of the drive member 16, characteristics of the extended and expanded end effector 50 may change. For example, due to the twisting of and/or torsion in the movable members 18, 20, and 22, when extended distally the movable members 18, 20, and 22 may expand radially outwardly from the longitudinal axis of the outer sheath 12 farther than they would with less of or without the twisting and/or torsion. As a result, with the end effector 50 extended and expanded and subject to twisting and/or torsion, the length of a radial line 74 extending from the longitudinal axis of the outer sheath 12 to the outermost point on any of the bridges 62, 64, and 66 in FIG. 6 may be greater than the length of a radial line 76 extending from the longitudinal axis of the outer sheath 12 to the outermost point on any of the bridges 62, 64, and 66 in FIG. 5 corresponding to the end effector 50 where the movable members 18, 20, and 22 are not subject to twisting and/or torsion. The perimeter of the front loop 60 in FIG. 6 may be greater than the perimeter of the front loop 60 in FIG. 5. The perimeters of the side loops 54, 56, and 58 in FIG. 6 may be greater than the perimeters of the side loops in FIG. 5.

Further, due to the twisting of and/or torsion in movable members 18, 20, and 22, the angle formed between portions of the movable members 18, 20, and 22 within the distal ends of the support members 26, 28, and 30 and the longitudinal axis of the outer sheath 12, when the basket is extended and expanded, may be greater than they would be with less of or without the twisting and/or torsion. Similarly, the angle formed between each of the distal ends of the support members 26, 28, and 30, and the longitudinal axis of the outer sheath 12, may be greater than it would be with less of or without the twisting and/or torsion.

Further, due to the twisting of and/or torsion in the movable members 18, 20, and 22, the end effector 50 in FIG. 6 may expand radially outwardly farther over less of an extension distance than the end effector 50 in FIGS. 4 and 5. For example, with reference to FIG. 4, when the movable members 18, 20, and 22 are twisted, the end effector 50 may reach full radial expansion at a first distance 78 from the distal end of the outer sheath 12. With less of or without the twisting and/or torsion, the end effector 50 may reach full radial expansion when extended a second distance 80 from the distal end of the outer sheath 12. The first distance 78 may be less than the second distance 80. Because the end effector 50 in FIG. 6 expands over a shorter distance, it may have the ability to grab bigger objects/more material earlier in its extension phase, and do so more securely because the movable members 18, 20, and 22 tend to lose strength the further out they are extended. As such, at full extension and expansion, the end effector 50 in FIG. 6 may be stronger than the end effector 50 in FIGS. 4 and 5. Shorter support members 26, 28, and 30 may be used for the basket in FIG. 6 than for the basket in FIGS. 4 and 5. A support member that is shorter is stronger than an support member that is longer. Shortening the support members 26, 28, and 30 may further strengthen the end effector 50 in FIG. 6. Accordingly, the user may be provided with enhanced control over the end effector 50 in FIG. 6 since it will better resist deformation under stress than the end effector 50 in FIGS. 4 and 5.

Further, since the end effector 50 in FIG. 6 fully expands over a shorter distance than the end effector 50 in FIGS. 4 and 5, a user may be able to index distances and/or sizes of objects in the target area because visualization aids at or near the distal end of the outer sheath 12 may be closer to the end effector 50 when it is extended and expanded. Furthermore, because the end effector 50 in FIG. 6 fully expands over a shorter distance, the end effector 50 in FIG. 6 may also contract over a shorter distance. Thus, the end effector 50 in FIG. 6 may be closed down on an object or material being retrieved faster than the end effector 50 in FIGS. 4 and 5. This may also provide the user with better control over the end effector 50, and/or the object or material.

It is contemplated that 1-2 rotations of the drive member 16 may be sufficient for creating the end effector 50 in FIG. 6, although it is possible that the number of rotations/partial rotations may vary based on properties of device components (e.g., movable member characteristics, support member characteristics, outer sheath characteristics, etc.). Rotation of the drive member 16 may also be adjustable based on how much basket expansion a user wants at one or more points during basket extension. Too much rotation may twist the movable members 18, 20, and 22 to a degree that prevents portions of the first legs 18a, 20a, and 22a from separating and entering the proximal ends of the support members 26, 28, and 30.

The direction of rotation of the drive member 16 that may enhance basket expansion may depend on the arrangement of the movable members 18, 20, and 22 in the support members 26, 28, and 30. For example, when the first leg 18a extends distally through the first support member 26, the second leg 18c extends proximally through the second support member 28, the first leg 20a extends distally through the second support member 28, the second leg 20c extends proximally through the third support member 30, the first leg 22a extends distally through the third support member 30, and the second leg 22c extends proximally through the first support member 26, rotating the drive member 16 in a first direction may increase twisting of the movable members 18, 20, and 22, and may increase torsion within the movable members 18, 20, and 22, causing the end effector 50 to expand in the manner shown in FIG. 6. Rotating the drive member 16 in a second direction (opposite the first direction) may not have that effect on expansion of the end effector 50.

On the other hand, when the first leg 18a extends distally through the first support member 26, the second leg 18c extends proximally through the third support member 30, the first leg 20a extends distally through the second support member 28, the second leg 18c extends proximally through the first support member 26, the first leg 22a extends distally through the third support member 30, and the second leg 22c extends proximally through the second support member 28, rotating the drive member 16 in the second direction may increase twisting of the movable members 18, 20, and 22, and may increase torsion in the movable members 18, 20, and 22, causing the end effector 50 to expand in the manner shown in FIG. 6. Rotating the drive member 16 in the first direction may not have that effect on expansion of the end effector 50.

FIGS. 8A-8D show the handle assembly 200. The handle assembly 200 may include a housing 202, an actuation assembly 204, a holding mechanism 216, and an end cap 206. The actuation assembly 204 (FIG. 8D) may include a body 208, and a protrusion 210 on an upper surface the body 208. The actuation assembly 204 may be at least partially received in a passage or cavity 212 of the housing 202. The cavity 212 may open into a longitudinal slot 222 running along an outer surface of the housing 202. The actuation assembly 204 may be slidable relative to the housing 202 within the cavity 212. For example, a user may grip the housing 202 in the palm of his/her hand, and may place his/her thumb on the protrusion 210. The user may push the actuation assembly 204 distally relative to the housing 202 by pushing the protrusion 210 with his/her thumb in a distal direction. The user may push the actuation assembly 204 proximally relative to the housing 202 by pushing the protrusion 210 with his/her thumb in a proximal direction.

Figure 8A:
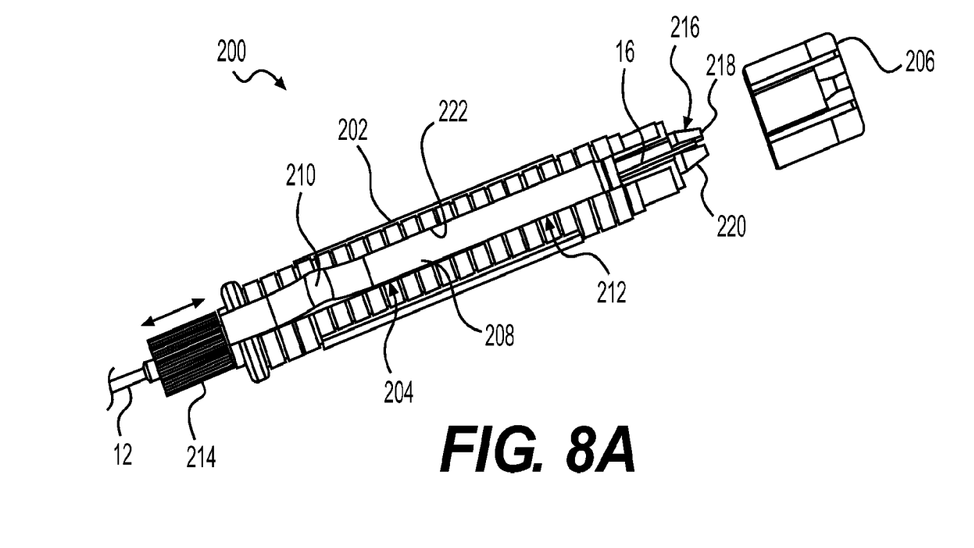
FIG. 8A is a perspective view of a handle assembly of the retrieval device of FIG. 1, in accordance with embodiments of the present disclosure.
Figures 8B, 8C:
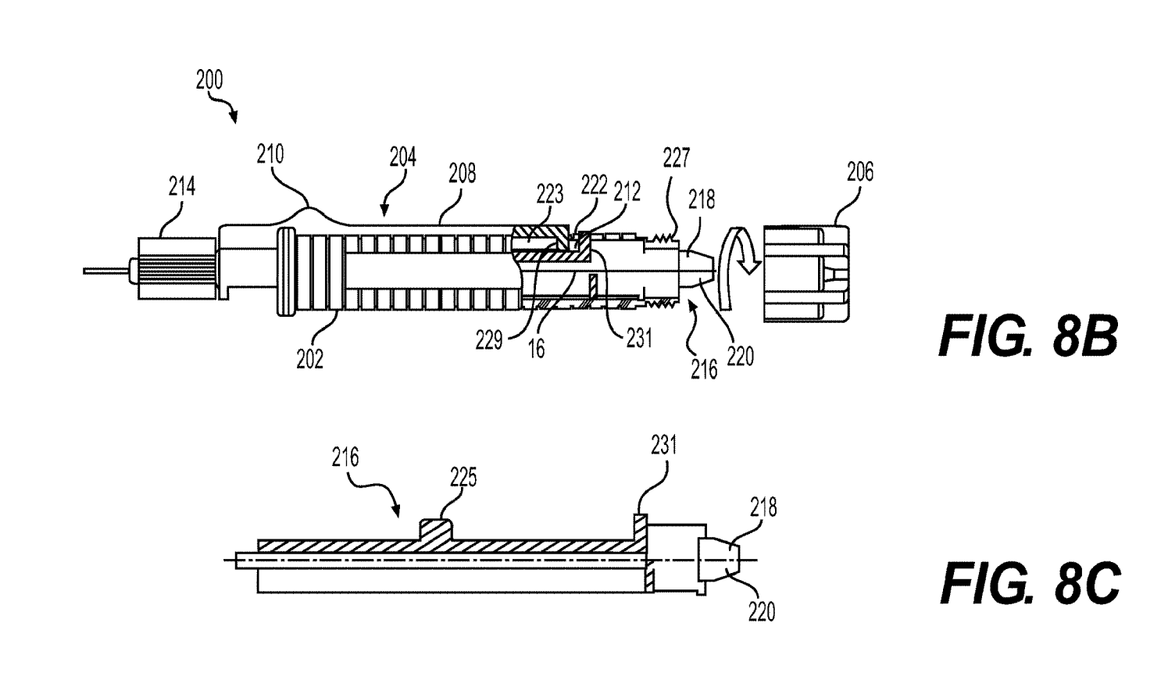
FIG. 8B is a side view of the handle assembly of FIG. 8A, in accordance with embodiments of the present disclosure.
FIG. 8C is a side view of a holding mechanism of the handle assembly of FIG. 8A, in accordance with embodiments of the present disclosure
Figure 8D:
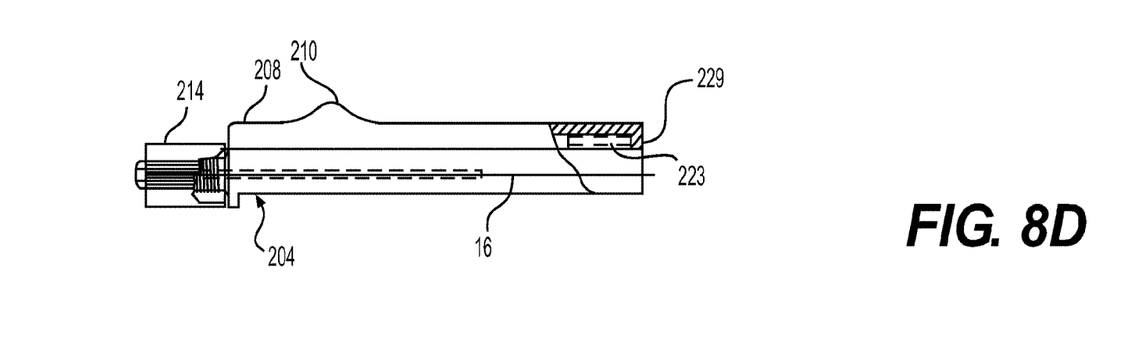
FIG. 8D is a side view of an actuation assembly of the handle assembly of FIG. 8A, in accordance with embodiments of the present disclosure.

A distal portion of the actuation assembly 204 may extend distally from the distal end of the housing 202. For example, the distal portion may extend out of an opening (not shown) at the distal end of the cavity 212. The distal portion may include a connector 214 configured to connect the outer sheath 12 to the body 208. The connector 214 may include, for example, a strain relief member. The outer sheath 12 may be moved distally relative to the drive member 16 (and the movable members 18, 20, and 22) by moving the actuation assembly 204 distally, and proximally by moving the actuation assembly 204 proximally.

The proximal end of the drive member 16 may extend through the handle assembly 200. The drive member 16 may extend through the cavity 212 or any other suitable opening or openings in the housing 202 and/or the actuation assembly 204. The housing 202 may receive a holding mechanism 216 (FIG. 8C). A proximal end of the holding mechanism 216 may include a vise, or any other suitable holding mechanism, that may extend proximally from the proximal end of the housing 202. The holding mechanism 216 may include a first jaw member 218 and a second jaw member 220. When the first and second jaw members 218 and 220 move toward one another, they may hold/clamp the drive member 16 between them, thus coupling the drive member 16 to the holding mechanism 216, and to the housing 202. The end cap 206 may help close the first and second jaw members 218 and 220 around the drive member 16 when the end cap 206 is placed over the proximal end of the housing 202. For example, the housing 202 may include an externally threaded portion 227. The end cap 206 may include complementary internal threading (not shown), and may be screwed onto the housing 202.

When the outer sheath 12 is moved distally by moving the actuation assembly 204 distally, the outer sheath 12 and support members 26, 28, and 30 may move distally relative to the housing 202, the drive member 16, and movable members 18, 20, and 22. The distally moving support members 26, 28, and 30 may slide over portions of the movable members 18, 20, and 22 forming the end effector 50, putting the end effector 50 in its retracted and contracted state. Moving the outer sheath 12 proximally by moving the actuation assembly 204 proximally may move the outer sheath 12 and support members 26, 28, and 30 proximally relative to the housing 202, the drive member 16, and movable members 18, 20, and 22. The proximally moving support members 26, 28, and 30 may slide off of or expose the portions of the movable members 18, 20, and 22 forming the end effector 50, allowing the end effector 50 to move to its extended and expanded state.

The amount of relative movement between the outer sheath 12 and support members 26, 28, and 30; and the drive member 16 and movable members 18, 20, and 22, may be set by engagement between portions of the actuation assembly 204 and the holding mechanism 216. For example, the holding mechanism 216 may include a proximal wall or protrusion 231 and a distal wall or protrusion 225. A proximal wall or protrusion 229 of the actuation assembly 204 may move proximally and distally in the space between the protrusions 225 and 231.

In one embodiment of the retrieval device 10, the end effector 50 may be in its retracted and contracted state (FIGS. 1-3) when the protrusion 229 of the actuation assembly 204 engages the protrusion 225 of the holding mechanism 216. The actuation assembly 204 move be moved proximally relative to the holding mechanism 216 and the housing 202, thus moving the outer sheath 12 and support members 26, 28, and 30 proximally relative to the drive member 16 and movable members 18, 20, and 22, and moving the end effector 50 into its extended and expanded state (FIGS. 4-6). Proximal movement of the actuation assembly 204 relative to the holding mechanism 216 and the housing 202 may halt when the protrusion 229 contacts the protrusion 231 of the holding mechanism 216. During this movement, the distance moved by the protrusion 229, in the space between protrusions 225 and 231, may produce distal movement of the first legs 18a, 20a, and 22a relative to the outer sheath 12 and support members 26, 28, and 30 over a distance including distances 49 and 51. The actuation assembly 204 may be moved distally relative to the holding mechanism 216 and the housing 202, until the protrusion 229 contacts the protrusion 225, to move the end effector 50 back into its retracted and contracted state. It is also contemplated that engagement between the protrusions 225 and 229 may help prevent the distal ends of the support members 26, 28, and 30 from being forced against the bends 18b, 20b, and 22b of the movable members 18, 20, and 22, during retraction/contraction of the end effector 50. Excessive force between the distal ends of the support members 26, 28, and 30 and the bends 18b, 28b, and 22b may cause splitting of the support members 26, 28, and 30.

In another embodiment of the retrieval device 10, the actuation assembly 204 may include a limiter 223 for limiting movement between the actuation assembly 204 and the holding mechanism 216. The limiter 223 may include, for example, a tube coupled to a distal face of the protrusion 229 of the actuation assembly 204. The end effector 50 may be in its retracted and contracted state (FIGS. 1-3) when the distal end of the limiter 223 engages the protrusion 225 of the holding mechanism 216. The actuation assembly 204 move be moved proximally relative to the holding mechanism 216 and the housing 202, thus moving the outer sheath 12 and support members 26, 28, and 30 proximally relative to the drive member 16 and movable members 18, 20, and 22, and moving the end effector 50 into its extended and expanded state (FIGS. 4-6). Proximal movement of the actuation assembly 204 relative to the holding mechanism 216 and the housing 202 may halt when the protrusion 229 contacts the protrusion 231 of the holding mechanism 216. During this movement, the distance covered by the protrusion 229 may be less than the distance covered by the protrusion 229 in the absence of the limiter 223, due to the length of the limiter 223 prepositioning the protrusion 229 farther proximally relative to the protrusion 225. The shortened distance may result in the distal movement of the first legs 18a, 20a, and 22a relative to the outer sheath 12 and support members 26, 28, and 30 over the distance 49, leaving the distance 51 unused. The actuation assembly 204 may be moved distally relative to the holding mechanism 216 and the housing 202, until the limiter 223 contacts the protrusion 225, to move the end effector 50 back into its retracted and contracted state.

In the embodiment that includes the limiter 223, only the distance 49 is normally used during extension/expansion and/or retraction/contraction of the end effector 50. If, however, an object captured in the end effector 50 is too large to be released from the end effector 50 by normal extension/expansion of the end effector 50, the user can remove the end cap 206 to free the drive member 216 from the holding mechanism 216. The user may then manipulate the drive member 216 manually in a distal direction relative to the actuation assembly 204, outer sheath 12, and support members 26, 28, and 30, over the distance 51, allowing for additional extension/expansion of the end effector 50 for releasing the object. Thus the limiter 223 and the distance 51 may provide an escape length of additional travel to help ensure that objects that may be small enough to be captured in the end effector 50, but too large to be readily removed from the end effector 50, may still be released. It is also contemplated that the engagement between the limiter 223 and the protrusion 226 may help prevent the distal ends of the support members 26, 28, and 30 from being forced against the bends 18b, 20b, and 22b of the movable members 18, 20, and 22. Excessive force between the bends 18b, 20b, and 22b and the distal ends of the support members 26, 28, and 30 may result in splitting of the support members 26, 28, and 30 during retraction/contraction of the end effector 50.

It is contemplated that the rotation 68 (FIGS. 6 and 7) may be applied to the drive member 16 by removing the end cap 206, taking hold of the proximal end of the drive member 16, rotating the drive member 16 in a desired direction through a desired rotation angle, and then closing the holding mechanism 216 around the rotated drive member 16 to keep the drive member 16 in its rotated state. The rotation 68 may provide the twist and/or torsion to the movable members 18, 20, and 22, so that the end effector 50 may be extended and expanded as shown in FIG. 6. The rotation 68 may be applied to the drive member 16 during manufacturing, such that the device may have a predetermined amount of rotation when it is received by a user.

Figure 9:
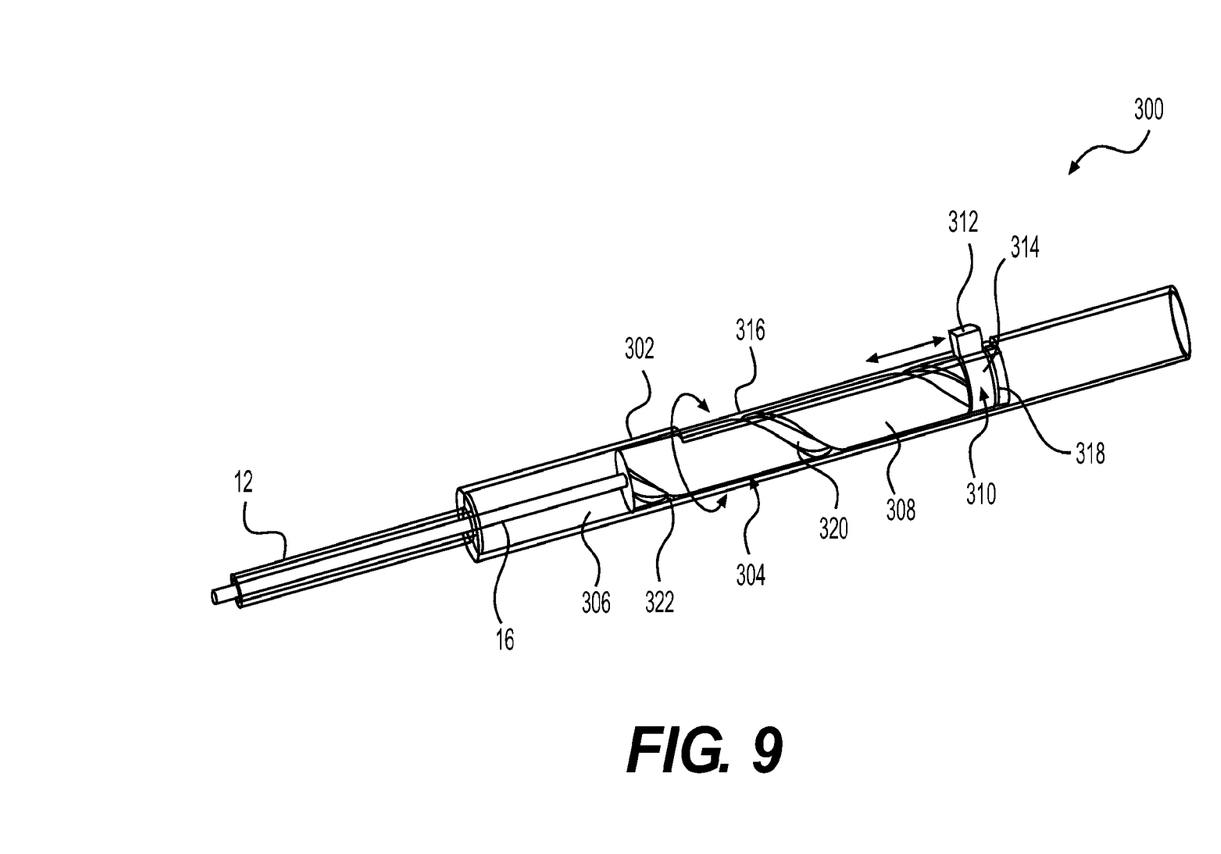
FIG. 9 is a perspective view of an alternative handle assembly of the retrieval device of FIG. 1, in accordance with embodiments of the present disclosure.

FIG. 9 shows another embodiment of a handle assembly 300. The handle assembly 300 may include a housing 302 and an actuation assembly 304. The actuation assembly 304 may include a body 308, and an actuation member 310 on the body 308. The actuation member 310 may include a protrusion 312 and a ring 314. The ring 314 may be received in a circumferentially extending slot 318 of the body 308. The body 308 and the ring 314 may be relatively rotatable. Relative longitudinal movement between the body 308 and the ring 314 may be limited or prevented due to engagement between proximal and distal surfaces of the ring 314 and proximal and distal surfaces of the slot 318.

The actuation assembly 304 may be slidably received in a lumen 306 of the housing 302. The protrusion 312 may be slidably received in a longitudinal slot 316 running along an upper surface of the housing 302. The actuation assembly 304 may be slidable relative to the housing 302 within the lumen 306. For example, a user may grip the housing in the palm of his/her hand, and may place his/her thumb on the protrusion 312. The user may push the actuation assembly 304 distally relative to the housing 302 by pushing the protrusion 312 with his/her thumb in a distal direction. The user may push the actuation assembly 304 proximally relative to the housing 302 by pushing the protrusion 312 with his/her thumb in a proximal direction.

The body 308 may include a keyway or slot 320 running along its length. The slot 320 may be in the shape of a spiral or helix. A key or protrusion 322 may extend radially inwardly from the interior surface of the housing 302. As the actuation assembly 304 moves proximally or distally, the key 322 may engage the slot 320, causing the body 308 to rotate. The actuation member 310 may be configured to not rotate with the body 308, due to the ring 314 being connected to, but freely rotatable relative to the body 308.

The distal end of the housing 302 may be coupled to the proximal end of the outer sheath 12. The proximal end of the drive member 16 may be coupled to the distal end of the body 308. Thus, the drive member 16 may be moved distally by moving the actuation assembly 304 distally, and proximally by moving the actuation assembly 304 proximally. The rotation 68 (FIGS. 6 and 7) on the drive member 16 may be applied to and/or increased by the rotation of the body 308 through engagement between the key 322 and the keyway 320 during distal movement of the actuation assembly 304. The rotation 68 may be decreased and/or removed from the drive member 16 by rotation of the body 308 through engagement between the key 322 and the slot 320 during proximal movement of the actuation assembly 304. With the embodiment in FIG. 9, the rotation 68 may be applied and/or increased while extending and expanding the end effector 50, and decreased and/or removed while retracting and contracting the end effector 50. It is contemplated that the orientation of the slot 320 (e.g., the direction of the spiral or helix) may be reversed to reverse the directions of rotation of the body 308 during proximal and distal movements of the actuation assembly 304. It is also contemplated that the amount of rotation 68 of the drive member 16 may be controlled by controlling the characteristics of the slot 320, such as the distance between its turns.

It is contemplated that the actuation assembly 304 may be coupled to the housing 302 by a mechanical fastening mechanism (not shown). The fastening mechanism may help keep the actuation assembly 304 in a position relative to the housing 302 when the actuation assembly 304 is not being moved by a user. The fastening mechanism may include, for example, friction fit engagement, a ratchet assembly, a latching assembly, or any other suitable fastening mechanism. Further, it is contemplated that in some embodiments, the fastening mechanism may act between the housing 302 and at least one of the body 308 and the actuation member 310.

Figure 10:
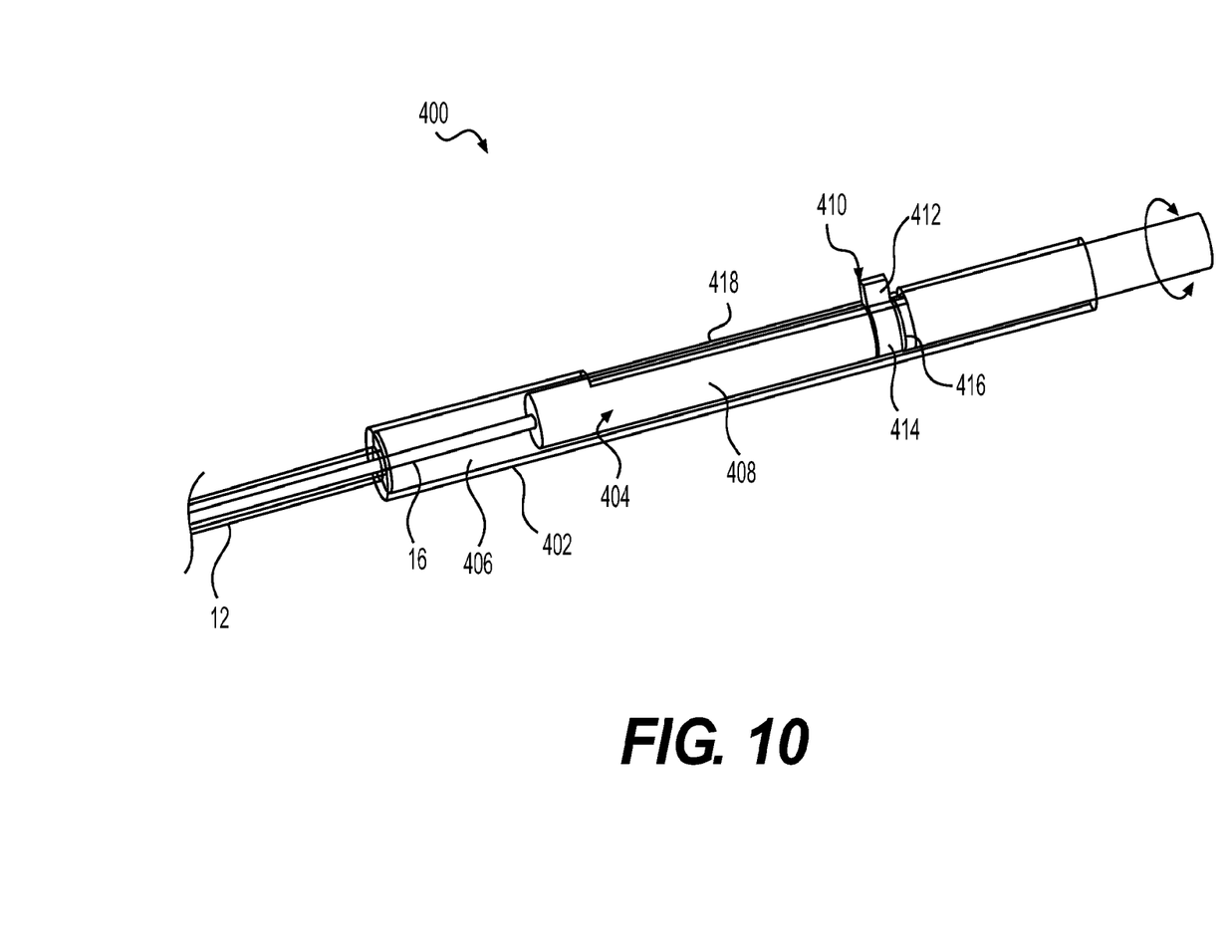
FIG. 10 is a perspective view of an alternative handle assembly of the retrieval device of FIG. 1, in accordance with embodiments of the present disclosure.

FIG. 10 shows another embodiment of a handle assembly 400. The handle assembly 400 may include a housing 402 and an actuation assembly 404. The actuation assembly 404 may include a body 408, and an actuation member 410 on the body 408. The actuation member 410 may include a protrusion 412 and a ring 414. The ring 414 may be received in a circumferentially extending slot 416 of the body 408. The body 408 and the ring 414 may be relatively rotatable. Relative longitudinal movement between the body 408 and the ring 414 may be limited due to engagement between proximal and distal surfaces of the ring 414 and proximal and distal surfaces of the slot 416.

The actuation assembly 404 may be received in a lumen 406 of the housing 402. The protrusion 412 may be received in a longitudinal slot 418 running along an upper surface of the housing 402. The actuation assembly 404 may be slidable relative to the housing 402 within the lumen 406. For example, a user may grip the housing in the palm of his/her hand, and may place his/her thumb on the protrusion 412. The user may push the actuation assembly 404 distally relative to the housing 402 by pushing the protrusion 412 with his/her thumb in a distal direction. The user may push the actuation assembly 404 proximally relative to the housing 402 by pushing the protrusion 412 with his/her thumb in a proximal direction.

The proximal end of the body 408 may extend proximally out of the housing 402. A user may grasp the proximal end of the body 408 and rotate the body 408 in clockwise and counterclockwise directions. The actuation member 410 may remain circumferentially set during rotation of the body 408, due to the ring 414 being freely rotatable relative to the body 408, and due to engagement between the actuation member 410 and the sides of the longitudinal slot 418.

The distal end of the housing 402 may be coupled to the proximal end of the outer sheath 12. The proximal end of the drive member 16 may be coupled to the distal end of the body 408. Thus, the drive member 16 may be moved distally by moving the actuation assembly 404 distally, and proximally by moving the actuation assembly 404 proximally. The rotation 68 (FIGS. 6 and 7) of the drive member 16 may be applied and/or increased by the user rotating the proximal end of the body 408 on one direction. The rotation 68 may provide the movable members 18, 20, and 22 with the twist and/or torsion for expanding the end effector 50 to the state shown in FIG. 6. The rotation 68 may be decreased and/or removed from the drive member 16 by the user rotating the proximal end of the body 408 in the opposite direction. With the embodiment in FIG. 10, the rotation 68 may be increased before, during, or after extending and retracting the end effector 50. It is contemplated that the body 408 may be selectively held in place by any suitable mechanical fastening mechanism, such as a friction fit assembly, ratchet assembly, or latching assembly.

The disclosed retrieval devices may be utilized in any suitable application requiring the capture and removal of materials from the body. Any aspect set forth in any embodiment may be used with any other embodiment set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

The disclosed devices may be configured to capture fragments having dimensions of about 3 French or smaller. In some embodiments, the disclosed medical devices may be able to capture and release smaller stones having diameters from 1 millimeter to 12 millimeters. In some embodiments, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and the retrieval device may be removed from the human body. In some embodiments, a guide sheath for a ureteroscope may be used to guide the ureteroscope and retrieval device back to a previous position or to a new position to capture additional stones, and protect a ureter wall during stone removal. While moving from the extended and expanded state to the retracted and contracted state, retrieval devices of the present disclosure may ligate larger stones and capture smaller stones within the end effector 50.

It will be apparent to those skilled in the art that various modifications and variations can be made in the disclosed systems and processes without departing from the scope of the disclosure. Other embodiments of the disclosure will be apparent to those skilled in the art from consideration of the specification and practice of the features disclosed herein. It is intended that the specification and examples be considered as exemplary only.

I claim:

1. A handle assembly comprising:
a housing coupled to an outer sheath including a lumen; and
an actuation assembly that is coupled to a drive member extending through the lumen, movably mounted to the handle assembly, and movable to translate and rotate the drive member independent of the outer sheath,
wherein a distal end of the outer sheath is coupled to a plurality of support members, and wherein each support member has a passage,
wherein a distal end of the drive member is coupled to a plurality of movable members, and wherein each movable member extends through one of the passages, and
wherein the drive member is rotatable relative to the plurality of support members to generate a torsion in the plurality of moveable members.

2. The assembly of claim 1, wherein the actuation assembly is movable to translate and rotate the drive member independent of the support members.

3. The assembly of claim 2, wherein the actuation assembly is movable to simultaneously translate and rotate the drive member independent of the support members.

4. The assembly of claim 1, wherein the torsion biases the plurality of moveable members towards a bent configuration.

5. The assembly of claim 4, wherein the outer sheath has a longitudinal axis, and each movable member extends radially outward from the longitudinal axis when the plurality of moveable members is in the bent configuration.

6. The assembly of claim 1, wherein the plurality of movable members and the plurality of support members form a plurality of loops.

7. The assembly of claim 6, wherein a distal end of each movable member is located proximal of each loop.

8. The assembly of claim 1, wherein the handle assembly defines a slot, and wherein the actuation assembly is slidable within the slot to translate the drive member.

9. The assembly of claim 8, wherein the actuation assembly is rotatable in the slot to rotate the drive member.

10. A handle assembly comprising:
a housing coupled to an outer sheath including a lumen and a plurality of support members; and
an actuation assembly that is movably mounted to the housing and coupled to a drive member extending through the lumen, the drive member including a plurality of moveable members extending through the plurality of support members, the actuation assembly being movable to translate and rotate the plurality of moveable members independent of the plurality of support members,
wherein a distal end of the outer sheath is coupled to the plurality of support members, and wherein each support member has a passage,
wherein each movable member extends through one of the passages of the plurality of support members, and
wherein the drive member is rotatable relative to the plurality of support members to generate a torsion in the plurality of moveable members.

11. The assembly of claim 10, wherein the actuation assembly is movable to translate the plurality of movable members without rotating said movable members.

12. The assembly of claim 10, wherein the actuation assembly is movable to simultaneously translate and rotate the plurality of moveable members.

13. The assembly of claim 10, wherein the drive member is rotatable to move the plurality of moveable members radially outward from a longitudinal axis of the outer sheath.

14. The assembly of claim 13, wherein the plurality of movable members and the plurality of support members form a plurality of loops including a distal front loop and a plurality of proximal side loops.

15. The assembly of claim 14, wherein at least the distal front loop expands in size when the drive member is rotated.

16. A handle assembly comprising:
a housing coupled to an outer sheath including a lumen; and
an actuation assembly that is coupled to a drive member extending through the lumen, movably mounted to the handle assembly, and includes:
(i) a longitudinal actuator movable to translate the drive member independent of the outer sheath, and
(ii) a rotational actuator movable to rotate the drive member independent of the outer sheath,
wherein a distal end of the outer sheath is coupled to a plurality of support members, and wherein each support member has a passage,
wherein a distal end of the drive member is coupled to a plurality of movable members, and wherein each movable member extends through one of the passages, and
wherein the drive member is rotatable relative to the plurality of support members to generate a torsion in the plurality of moveable members.

17. The assembly of claim 16, wherein the longitudinal actuator is movable independent of the rotational actuator.

18. The assembly of claim 16, wherein the longitudinal actuator is movable together with the rotational actuator.

* * * * *